(12) United States Patent
Thibiant et al.

(10) Patent No.: US 6,245,344 B1
(45) Date of Patent: Jun. 12, 2001

(54) ENHANCED SPIRAL COMPOSITIONS

(75) Inventors: Patrick Thibiant, 1475 Via Cresta, Pacific Palisades, CA (US) 90272; Daniel Long, Simi Valley, CA (US); Moe Witwit, Northridge, CA (US)

(73) Assignee: Patrick Thibiant, Pacific Palisades, CA (US)

( * ) Notice: Subject to any disclaimer, the term of this patent is extended or adjusted under 35 U.S.C. 154(b) by 0 days.

(21) Appl. No.: 09/362,764

(22) Filed: Jul. 28, 1999

(51) Int. Cl.[7] .............................. A61K 7/00; A61K 7/42; A61K 9/00
(52) U.S. Cl. ..................... 424/401; 424/400; 424/59; 514/844; 514/847; 514/937
(58) Field of Search ............................ 424/59, 400, 401; 514/844, 847, 937

(56) References Cited

U.S. PATENT DOCUMENTS

| | | |
|---|---|---|
| 3,479,429 | 11/1969 | Morshauser et al. . |
| 3,980,767 | 9/1976 | Chown et al. . |
| 4,159,028 | 6/1979 | Barker et al. . |
| 4,335,103 | 6/1982 | Barket et al. . |
| 4,425,322 | 1/1984 | Harvey et al. . |
| 4,438,095 * | 3/1984 | Grollier et al. ........................ 424/70 |
| 4,966,205 | 10/1990 | Tanaka . |
| 4,980,155 | 12/1990 | Shah et al. . |
| 5,059,414 | 10/1991 | Dallal et al. . |
| 5,165,917 * | 11/1992 | Zabotto et al. ........................ 424/70 |
| 5,213,799 * | 5/1993 | Goring et al. ........................ 424/401 |
| 5,290,555 * | 3/1994 | Guthauser et al. .................. 424/401 |
| 5,304,334 | 4/1994 | Lahanas et al. . |
| 5,468,496 * | 11/1995 | Touzan et al. ....................... 424/401 |

* cited by examiner

Primary Examiner—Shelley A. Dodson
Assistant Examiner—Marina Lamm
(74) Attorney, Agent, or Firm—Pillsbury Winthrop LLP

(57) ABSTRACT

A dual phase product is comprised of at least a first phase colored with an effective amount of a coloring agent to contrast with at least a second phase, whereby said at least a first phase is disposed to form a visually attractive pattern within said at least a second phase, and such pattern may be viewed through a container housing the novel composition of the present invention and its enhanced spiral means.

23 Claims, No Drawings

ENHANCED SPIRAL COMPOSITIONS

CROSS-REFERENCE TO RELATED APPLICATIONS

U.S. Ser. No. 29/103707, filed Apr. 20, 1999 is expressly incorporated herein by reference, the application covering the ornamental appearance of subject spiral compositions invented by the present inventors and subject to an assignment to the present assignee.

BACKGROUND OF THE INVENTION

Area of the Art

The present invention relates to dual phase products. In particular, the present invention relates to a spirally disposed dual phased composition.

Description of the Prior Art

There are thousands of facial/body gels and facial/body lotions. Some of these products are good and some are bad. Making a two-or-more-phase product in one dispensing container can be very difficult and sometimes impossible due to chemical reactions or product instability (i.e., reacting with each other).

There has been a longstanding need to overcome the inability to effectively combine multi-phase products in a single container. This issue is based in large part on the chemical and the system chemistry and incompatibility; for example, putting water and oil together. After reviewing thousands of products, we have not seen a composition effective for use as a personal care product with two or more phases disposed in one dispensing container.

Part of the reason for this is that, generally, cosmetic materials may contain various types of coloring materials such as pigments and dyes. Such coloring materials are in some cases contained as masking agents for covering coloring derived from raw materials and are in some cases contained for the purpose of providing a particular effect in relation to skin makeup which is a positive function of those coloring materials.

Since consumers have recently shown an increasingly diverse sense of appreciation in regard to the value of cosmetic material, however, cosmetic materials of this kind are now required to possess certain additional merits related to their intrinsic appeal as objects of beauty which provide pleasure in use, as well as their basic functions of being useful and effective.

One known attempt to overcome this problem involved making a main cosmetic material transparent and forming a three-dimensional pattern in the transparent cosmetic material by using coloring materials. As explored further below, this did not work as expected, and has not adequately addressed the problem solved by the present invention.

Another example is found in the preparation of two or more differently colored products such as lipsticks, with the goal being to produce a two-tone or multi-colored effect on the lips. In such instances, to achieve the desired blending effect, one color is usually applied to the lips as a base and the other color or colors superimposed thereon for contrast. The desired final effect is then achieved by blending the superimposed colors while on the lips.

Likewise, attempts have been made to produce a unitary lipstick having a plurality of colors by assembling several individual segments in side-by-side relationship and thereafter pressing the segments together to form a unitary lipstick mass. Such lipsticks, however, have met with limited commercial success and one reason may be that these lipsticks have been more difficult and expensive to produce than conventional one-color lipsticks. In practice, of course, lipsticks which are formed by molding segments of different colors into a single multi-colored tube are usually applied to the lips by using the single color of each segment such that these lipsticks merely offer the convenience of two separate colors in one unitary mass.

Thus, the problem of making a duophase or multiphase cosmetic composition has remained prominent. Inasmuch as such a composition has a potential for combining two or more functional cosmetic compositions into a single product that may be applied to a subject's face or both in one application, the commercial need for the same is ongoing.

However, with any such multifunctional, multiphase cosmetic composition it is obviously important that the formed product be functional and effective and that such be maintained, preserved, and usable over a reasonable product life span.

One particular area of concern is in containerizing and packaging a multiphase cosmetic composition. Here, it is desirable that each of the phases comprising the total product be dispensed into a container such that the respective phases are generally maintained separately, remain stable, and that in viewing the product each phase, as packaged, is visually distinct. Of principal concern is that during the proposed life of a multiphase cosmetic product, respective phases comprising the total product do not blend and mix together such that the total product in the end is nearly or substantially homogeneous.

In addition, in containerizing a multifunctional, multiphase cosmetic composition, it is important that the respective phases comprising the composition be dispensed in a manner such that the particular phases are present and occur throughout the final product such that in gathering a single application from a container, the subject is likely to gather an adequate amount of each respective phase.

Related color-based issues must also be addressed. Many cosmetic products rely on color to provide beauty enhancement. Thus, such beauty aids as foundation, blush, mascara, brow products and the like rely on color enhancement provided by these products for effectiveness. In view of the criticality of color in such applications it is desirable to present the cosmetic product, which is ultimately applied to the face or other parts of the body to highlight that color, in a way that emphasizes its color. In the past such cosmetic products, if visible at all, were presented as a colored composition. Those skilled in the cosmetic arts appreciate that if the color of the cosmetic composition could be presented in a more dramatic manner, the product would be more desirable to the purchaser. For example, presenting the color in the form of a spiral, swirl or the like, against a background of a clear or color contrasted liquid dramatically emphasizes the attractiveness of the color of the cosmetic beauty aid.

It would be relatively simple to produce an oil-based pigment phase in a clear aqueous phase or vice versa. The immiscibility of the two phases would permit the production of a cosmetic product in which the above desired, highly attractive packaging could be provided. However, the inclusion of an oil-based phase would be undesirable for at least two reasons. First, it would be difficult to combine the immiscible phases to form the complete cosmetic composition. Second, even if the two immiscible phases could somehow be combined, the product, containing a non-water-soluble phase might be difficult to remove.

Ideally, a two-phase composition should include a color phase and clear or color contrasted gel phase which are miscible. However, when attempts were made to produce such a product in the past, a two-phase composition was obtained in which the color phase bled into the gel phase, producing a product that was aesthetically unattractive.

Thus, cosmetic products have not been produced in which a color phase, highlighting the tint or color of the cosmetic composition, is disposed as a discrete color phase against a background of a clear or color contrasted gel.

To compound the problem, conventional cosmetic vehicles for skin moisturization deliver moisture to the skin only on the initial application of the cosmetic moisturizer. The need for a cosmetic, dermatologic or medicinal multiphasic vehicle that will, in addition, provide sustained skin moisturization while blocking skin moisture loss has been long felt. There has also been a need for a multiphase vehicle that can be used to provide water-soluble and lipid-soluble active ingredients, such as vitamins, plant extracts, antioxidants, proteins, polymers, oils and the like. Most cosmetic vehicles consist of emulsions.

An emulsion is known to be a dispersed system comprising at least two immiscible liquid phases (*Remington's Pharmaceutical Sciences,* 18th Edition, 1990). The emulsion's immiscible liquid phase is composed of droplets between 0.005 to 2000 microns in diameter, although the range of droplet diameters may be narrower (e.g., between 0.1 to 100 microns). Emulsions are known to be thermodynamically unstable. It is believed that the free energy associated with high surface area of small droplets is reduced when these droplets coalesce into large droplets of less surface area. To minimize droplet coalescence, it is known that an emulsifying agent can be added to form a thin film about each droplet of immiscible liquid in the emulsion (*Remington's Pharmaceutical Sciences,* 18th Edition, 298–309, 1990).

Perfluoropolyethers (PFPE) such as perfluoropolymethylisopropyl ether (Montefluos trade name Fomblin HC) are useful as non-greasy lubricants. These compounds are odorless, colorless, tasteless, nonvolatile, nontoxic, and chemically stable below 300° C. Consequently, PFPEs with a molecular weight between 250 to about 30,000 have been used in a wide variety of cosmetic formulations for make-up, hair, toiletry, skin and baby products (Brunetta F., et al., *Cosmet. Toilet, Ital.* Edition 2, March/April 1986; Brunetta F., et al.; *XIV Congreso L F.S.C.C.* Barcelonea, Spain Volume 1:513, Sep. 16–19, 1986).

PFPEs are known additives to multiphase emulsions due to their tendency to form thin films. "Perfluoropolyethers For Cosmetics", D&CI, September 1988, 34–35, 116, 119, disclose the use of perfluoropolyethers (in particular, Fomblin) in cosmetics in which the insolubility of Fomblin is asserted not to affect the preparation of stable emulsions. It is further disclosed that the use of 0.1–3% Fomblin HC in oil-in-water emulsions produces finer dispersions and that 02–1.0% of Fomblin HC/25 increases the moisturizing properties of creams. Finally, the article states that all grades of Fomblin HC form a "thin and non-occlusive film, providing a satin finish and skin feel" (Ibid. at p. 119; see, also, Bader S, et al., Montefluos SpA Company bulletin). U.S. Pat. No. 4,803,067 discloses the utility of perfluoropolyethers not only as waterproofing agents but also as a barrier against loss of moisture from the skin without adversely affecting skin respiration.

It is also known that emulsions of PFPE can be used to protect human and animal skin against toxic agents such as mineral acids, caustic alkali, and organic solvents such as toluene and kerosene (Morganti P & Randazzo, *J. Appl. Cosmetol.* S. D. 7:23–30, 1989).

Stable emulsions containing silicones of two or three phases are well-known. The low surface tension of silicone promotes thin film formation which stabilizes emulsions. Lower alkyl ($C_1$–$C_4$) and amino-substituted polysilaxanes (silicones) are used because of their insolubility in polar and non-polar liquids such as water and oils. Seldom used are the cyclic silicones such as diphenylmethicone because of their oil solubility which causes the cyclic silicones to dissolve in the oil phase of the emulsion rather than forming a distinct phase.

Silicone emulsions have been used in a number of products. In cosmetic, pharmaceutical and skin preparations, a fat paste-like emulsion of decamahylpentasilaxune, poly (oxyethylene stearate), water and sorbitan monostearate has been used (Thimineur R. J. & Traver F. J., DE 3,045,083). In personal-care formulations, such as water-based hair conditioners, a water in silicone emulsion has been used (Gum, M. L., WO8S/03641/AI). In formulations for polishes, an emulsion of dimethylsiloxanes, naphtha hydrocarbons, emulsifiers and water has been used (Hill M. P. L. & Vandamme L. J R., DE 3,616,575 Al). Water-thinned paint emulsions have used silicones (Udalova A. V., et al., Lakokas Mater, Ikh. Primen., 2:14–16). Waterproof sealant emulsions have used silicones (Saad W. T. & Stodgell R. F., U.S. Pat. No. 4,383,062; Bauman T. M., Freiberg A. L., U.S. Pat. No. 4,590,220).

The ordered phase of liquid crystal has many of the properties of the solid state such as optical anisotropy and birefringence which produce special interference patterns that can be detected using a cross polarizing microscope. Liquid crystals also have the mechanical properties of liquids. Because the crystals have only partial rotational or translational freedom the liquid crystals exist in a mesophase state (*Intro to Liquid Crystals,* Priestly E. B., et al., editors, Plenum Press, N.Y. 1976).

Liquid crystals known as Iyotropic liquid crystals may spontaneously form when the concentration of oils in an oil-water emulsion is at a particular concentration. (See, e.g., Marland J. S. & Mulley B. A., *J. Pharm. Pharmocol.* 1971, 23(8): 561–572). Lyotropic liquid crystal formation is commonly observed in a wide variety of emulsions and such liquid crystals are known to be unstable.

There are likewise liquid crystals that are known to form at only certain temperatures known as thermotropic liquid crystals. This type of liquid crystals is quite stable.

Accordingly, each phase must maintain certain chemical and physical properties, which makes each phase stable and gives them the ability to co-exist with the other. The physical properties are very important in terms of dispensing. Maintaining a certain viscosity and specific gravity (density) allows us to have a more stable and functional product. The viscosity is one of the most important physical properties. Each product must maintain a certain viscosity. The viscosity for each product must be close to the other. The viscosity difference between each phase must be maintained within a certain range, which is relative to the rheology of the product. Thus, it is extremely critical that each product have similar rheology, i.e., thixotropic with thixotropic. Maintaining similar rheology will enable us to dispense the product evenly when energy is applied. Furthermore, it will enhance the product shelf life by preventing the multiple phase product from mixing with each other.

The chemical properties are as important, if not more so, than the physical properties. Having different chemical properties, using different chemicals, or even using the same charged product (i.e., cationic with cationic) will allow us to have a more stable product. Attempts have been made to use different emulsion systems with different aqueous and anhydrous gel systems.

Likewise prior art attempts have incorporated the carbomer, polymer, crosspolymer, silicone, humectant, elastomer dispersion, lubragel polytrap and different emulsion (i.e., hydrophillic, hydrophobic) chemistry in delivery systems, where filling of product played a major role in the outcome of the finished product. The different designs or the fill ratio of each phase was hoped to address different needs and applications; for example, dry skin, oily skin, and the like.

In cosmetic emulsions that are applied to the skin, water and active ingredients ("actives") such as vitamins, oils, antioxidants and the like are released from their respective phases in the emulsion by diffusion. A product for external use having multiple discontinuous phases can serve a number of important functions. Each phase can function as an independent delivery system for moisturizers, emollients, bioactive materials, and the like.

The release of material from the dispersed phase, and its subsequent absorption into the stratum corneum, are critically dependent on the interaction between the material, its solvent, and its immediate interface (Zatz J. L., Cueman G. H., *J. Soc. Cosmet. Chem.* 39:211–222, 1988). The complexity of these interactions usually increases with the number of phases. This makes multiple emulsions excellent candidates for tailored-release systems, as exemplified by their use in the administration of vaccines, drugs, and anticancer agents (Becher P., *Encyclopedia of Emulsion Technology*, pp. 199–202, Marcel Dekker, N.Y. 1985).

Phase inversion occurs when an oil/water emulsion changes (inverts) to a water/oil emulsion. Inversion can be induced by adding electrolyte, changing the ratio of the phase volumes, cooling a heated emulsion, adjusting the amount of emulsifier, or when the dispersed phase exceeds 50% of the total volume of the emulsion (Remington's *Pharmaceutical Sciences, pp.* 307–308, 1990).

By way of further background, attention is called to the following United States Letters patent references each of which has been found to be distinguishable from the teachings of the present invention, yet representative of at least one aspect of the state of the art:

U.S. Pat. No. 5,304,334 issued Apr. 19, 1994 to Lahanas et al., and assigned to Estee Lauder, Inc., for a Method of Preparing a Multiphase Composition;

U.S. Pat. No. 5,059,414 issued Oct. 22, 1991 to Dallal et al. and assigned to Shiseido Co. Ltd., for Multi-Phase High Viscosity Cosmetic Products;

U.S. Pat. No. 4,980,155 issued Dec. 25, 1990 to Shah et al. for a Two Phase Cosmetic Composition;

U.S. Pat. No. 4,966,205 issued Oct. 30, 1990 to Tanaka and assigned to Pola Chemical Industries for a Method and Apparatus for Charging Transparent Material;

U.S. Pat. No. 4,425,322 issued Jan. 10, 1984 to Harvey et al. for Dual Action Dentrifirce;

U.S. Pat. No. 4,335,103 issued Jun. 15, 1982 to Barker et al., and assigned to Almay, Inc. for a Multiphase Cosmetic Composition and your attention is directed to Column 6, lines 46–66;

U.S. Pat. No. 4,159,028 issued Jun. 26, 1979 to Barker et al., and assigned to Almay, Inc., for a Method of Forming and Containerizing a Multiphase Cosmetic Composition;

U.S. Pat. No. 3,980,767 issued Sept. 14, 1976 to Chown et al., and assigned to Beechum Group Limited, for Gel Toothpastes; and U.S. Pat. No. 3,479,429 issued Nov. 18, 1969 to F. S. Morshauser et al. for a Multi-Colored Cosmetic Preparation.

It should be noted that U.S. Pat. No. 4,335,103 to Barker et al. discloses a two-phase cosmetic cleansing cream composition which includes two separate and stable cosmetic composition phases which, when intimately mixed, yield a cleansing composition that is applicable to the face and other parts of the body.

This composition further comprises a first cleansing cream phase composition which includes an oil, a thickening agent, an emulsifier and water. The second phase, a gel phase, comprise water or a water soluble material and a thickening agent. The two-phase cosmetic cleansing cream compositions are combined in a swirl-like or marble-like pattern within a container such that the cream hard gel phases are generally stable, separate and visibly distinct.

Although the teaching of the '103 patent represents an advance in the art, it does not emphasize a color phase. Colorants easily migrate. As such, the absence of a teaching in the prior art of non-bleeding phases establish the absence in the art of a two-phase cosmetic composition in which the color phase composition highlights the critical emphasis of the composition of the present invention.

Clearly, there is a longstanding need for a new composition that can be used with a delivery system for cosmetics such that a dual spiral product or dual phase product housed in one container, maintaining desired ornamental appeal while preserving for dispensation desired product attributes and utilities.

SUMMARY OF THE INVENTION

Accordingly, it is a prime object of the present invention to provide a product that overcomes the drawbacks of the prior art.

Additionally an important object of the present invention is to provide a gel system (aqueous) based on carbomer, lubragel, polymer, and different humectant chemistry to give different textures and, equally as importantly, product stability, using conventional coloring agents to create a visually attractive appearance.

Yet another object of the present invention is provision of a system which yields a great functionality level in combination with a visually appealing product, by employing known coloring means in combination with a novel chemical composition effective for creating visually perceptible spirals, helices, and the like features effective for use as disposed within an at least partially transparent container.

Likewise, according to the present invention an object is provision of a novel spiral composition which is a stable and extremely functional product for different cosmetic based applications, including as a therapeutic skin composition for those whose skin is in need of such therapy or sensitive to the same.

Briefly stated, a dual phase product is comprised of at least a first phase colored with an effective amount of a coloring agent to contrast with at least a second phase, in a ratio of from about 10:1 to about 1:10, whereby said at least a first phase is disposed to form a visually attractive pattern within said at least a second phase, and such pattern may be viewed through a container housing the novel composition of the present invention and its enhanced spiral means.

The foregoing and other objects of the invention are achieved by a composition contained in a single generally transparent container, said composition comprising at least two separate substantially dispersed phases which may include at least one water continuous phase and at least one oil continuous phase selected to maintain a visually perceptible pattern, which may include a spiral or an abstract, over a period of time, which may be 3–6 months. At least a first phase is colored with an effective amount of a coloring agent to contrast with at least a second phase, whereby said at least a first phase is disposed to form said pattern within said at least a second phase, in a ratio of from about 10:1 to about 1:10, and preferably from about 3:2 to about 2:3, whereby said pattern is observable through said container.

The coloring agents may include colored mica, chlorophyll, carrot oil, and metallic based, i.e., copper, zinc, chromium, manganese, and iron, colorants as are well known in the art.

The composition can be therapeutic skin compositions containing an effective amount of at least one dermatologically active ingredient for treating the skin of an individual whose skin is in need of such therapy. Alternatively, moisturizing and conditioning skin compositions containing an effective amount of at least one moisturizing and conditioning ingredient for treating the skin of an individual whose skin is in need of moisturizing and conditioning represent another embodiment. Still another aspect of the invention is shampoo compositions for application to the hair and scalp of an individual in need of such application. The shampoo compositions may be therapeutic shampoo compositions containing an effective amount of at least one therapeutically active ingredient for treating the scalp of an individual whose scalp is in need of such therapy. Further aspects are conditioning shampoo compositions containing an effective amount of at least one conditioning ingredient for conditioning the hair of an individual whose hair is in need of conditioning. Still further aspects are coloring shampoo compositions containing an effective amount of at least one coloring ingredient for coloring the hair of an individual whose hair is in need of coloring.

The therapeutic skin compositions may include vitamins, antioxidants, hormones, anesthetics, antimicrobials, antipsoriatic agents, anti-acne agents, scabicides, pediculocides, keratolytics, sunscreens, agents to increase pigmentation, agents to decrease pigmentation, and skin protectants. The moisturizing and conditioning skin compositions may include vitamins, antioxidants, pH modifying agents, moisturizing agents, astringents, skin lubricants, humectants, and emollients. The therapeutic shampoo compositions may include vitamins, antioxidants, hormones, antimicrobials, antipsoriatic agents, scabicides, pediculocides, and keratolytics. The conditioning shampoo compositions may include vitamins, antioxidants, pH modifying agents, moisturizing agents, lubricants, humectants, and emollients. The coloring shampoo compositions may include at least one coloring ingredient selected from the group consisting of synthetic hair dyes, plant derived hair dyes, hydrogen peroxide solution, and pH modifying agents.

Another aspect of the invention is a method for treating skin comprising the application of a skin composition containing an effective amount of at least one ingredient selected from the group consisting of vitamins, antioxidants, hormones, pH modifying agents, moisturizing agents, astringents, anesthetics, antimicrobials, antipsoriatic agents, anti-acne agents, anti-dandruff agents, scabicides, skin lubricants, pediculocides, keratolytics, sunscreens, agents to increase pigmentation, agents to decrease pigmentation, skin protectants, and emollients for treating the skin of an individual whose skin is in need of treatment, wherein said composition is contained in a single generally transparent container, said composition comprising at least two separate substantially dispersed phases, wherein at least a first phase is colored with an effective amount of a coloring agent to contrast with at least a second phase, whereby said at least a first phase is disposed to form a visually perceptible pattern within said at least a second phase, whereby said pattern is observable through said container.

Still another aspect of the invention is a method for treating skin dryness, comprising the application of an effective amount of a composition of the invention wherein at least one therapeutically active ingredient is selected from the group consisting of moisturizing agents and skin lubricants, to the skin of an individual whose skin is dry. Yet still another embodiment is a method for treating scalp ailments, comprising the application of an effective amount of a composition of the invention, wherein one therapeutically active ingredient is selected from the group consisting of antipsoriatic agents, scabicides, pediculocides, and keratolytics, to the scalp of an individual with a scalp ailment. Yet still another embodiment of the invention is a method for conditioning the hair, comprising the application of an effective amount of a composition of the invention for washing the hair of an individual whose hair requires conditioning. Likewise, a method for coloring the hair, comprising the application of an effective amount of a composition of the invention for washing the hair of an individual whose hair requires coloring.

An article of manufacture, comprising packaging material and a composition of the invention contained in a single generally transparent container, said composition comprising at least two separate substantially dispersed phases selected to maintain a visually perceptible pattern over a period of time, wherein at least a first phase is colored with an effective amount of a coloring agent to contrast with at least a second phase, whereby said at least a first phase is disposed to form said pattern within said at least a second phase, in a ratio of from about 10:1 to about 1:10, and preferably from about 3:2 to about 2:3, whereby said pattern is observable through said container is also taught.

According to another feature of the invention there is provided an article of manufacture comprising; at least partially transparent packaging housing at least two separate dispersed phases, wherein at least a first phase is colored with an effective amount of a coloring agent to contrast with at least a second phase, whereby said at least a first phase is disposed to form a visually attractive pattern within said at least a second phase, whereby said pattern is observable through said at least partially transparent packaging material.

According to yet still an additional feature of the invention there is provided a therapeutic skin composition containing an effective amount of a least one therapeutically active ingredient for treating the skin of an individual whose skin is sensitive to such therapy, said composition contained in a transparent container, said composition comprising at least two separate dispersed phases, wherein at least a first phase is colored with an effective amount of a coloring agent to contrast with at least a second phase, whereby said at least a first phase is disposed to form a visually attractive pattern within said at least a second phase, whereby said pattern is observable through said container.

DETAILED DESCRIPTION OF THE INVENTION

The present inventors have discovered that they can provide a dual phase, or dueling spiraled product housed in one container which is both visually attractive and functional.

A first example for the Dual Spiral Product according to a preferred embodiment of the present invention, comprises first a Gel Phase, and according to the instant teachings a clear gel phase can have either an:

i. Aqueous System; or an
ii. Anhydrous System.

An Aqueous System according to the teachings of the present invention consists mainly of the oldest and the best moisturizing agent—water. Water is the most important hydrating ingredient for the skin. The gel system we have created consists of adequate levels of humectant (humectant has an affinity for water).

In addition to the humectant, there are balanced levels of skin moisturizers and conditioners to maintain a healthy, glowing skin. The gel system will always maintain a clear appearance. The clear appearance will create a great visual effect on the finished product. The gel system will normally come in different colors, different chemicals and physical properties. The different colors will give us the possibilities to call out certain flavors and actives (i.e., extracts, moisturizers, etc.). Having different chemicals and physical properties allows us to create numerous personal care products (i.e., facial and body treatments, cationic, non-ionic, etc.). Clear aqueous gel systems normally have excellent hydrating and moisturizing properties.

A preferred embodiment of a gel system (aqueous) is based on carbomer, lubragel, polymer, and different humectant chemistry to give us different textures and, most importantly, product stability. An Ahydrous System, according to the teachings of the present invention, is comprised of non-aqueous thickeners, and those skilled in the art will readily understand agents that function effectively within this context.

A Lotion Phase or Emulsion, further comprises, at least one of:

iii. Water In Oil Emulsion;
iv. Water In Oil With Water Resistance Emulsion;
v. Oil in Water Emulsion;
vi. Water In Silicone Emulsion;
vii. Silicone In Water Emulsion; and
viii. Multiple Phase.

As indicated, according to a preferred embodiment a lotion phase has multiple possibilities with known emulsion systems as indicated. Multiple possibilities and embodiments are offered for the Lotion Phase to provide a wide variation of products and, most importantly, enhanced stability.

A particularly preferred embodiment above listed Romanette ii. We have selected the water in oil with water resistance emulsion to enhance the product stability to co-exist with another product.

The emulsion system we have developed contains essential refatting ingredients. This system contains the proper essential vitamins, humectants, and conditioners. We have used polymer, carbomer, crosspolymer, silicone and polytrap chemistry. The combination of these ingredients allows us to develop a wide variety of products with different physical and chemical properties.

A second example is a Dual Spiral Product Gel/lotion Combination. As discussed, we have developed a unique delivery system by filling two completely different products (chemical properties) in the same container. The product is designed to give us:

ix. A visually appealing product.
x. A unique delivery system that enables each product to compliment the other.
xi. The ability to work with a wide variety of products with unstable or hard to formulate chemicals (i.e., ascorbic acid).
xii. A multiple functioning product (i.e., a moisturizing and conditioning clear alcoholic gel with a high fragrance level).

As indicated above, a wide variety of functions are attained according to the instant teachings. The system has an additional unique property in that it entraps moisture (from the gel) on the skin and protect the skin with the water-resistant lotion, in addition to working in combination with know coloring agents, as will be clear to artisans.

According to this preferred embodiment, the product delivers immediate moisturizing, conditioning, and refatting properties, depending on the fill ratio of the two products, which makes it very interesting. By having different ratios of the two products, we can address different needs, applications and skin types.

Finally, according to this preferred embodiment the system optionally has multiple phases (more than two). The combination of products which may be generated for separate cosmetic applications is therefore de-limited.

Set forth hereafter are Table 1 and Table 2, further comprising specific formulations of dual phase compositions according to the instant teachings. Table 1 includes product specifications for a Dual Spiral Body Lotion, while Table 2 is a Spiral Product which is ideally suited for use as a Body Lotion.

It is noted that U.S. Ser. No. 29/103707, filed Apr. 20, 1999 is expressly incorporated herein by reference, the application covering the ornamental appearance of subject spiral compostions invented by the present inventors and subject to an assignment to the present assignee.

Likewise, the composition of the present invention has been used to generate a plurality of related ornamental designs, ranging from basic spiral configurations to doubles helices, twisted and inverted helices and the like novel enhanced visually pleasing product configurations. It is noted that an additional and important attribute of the instant teachings is the durability of the subject designs, which are currently being produced, tested, and formulated (Thibiant International, 8601 Wilshire Boulevard, Suite 110, Beverly Hills, Calif. 90211) with an ability to withstand the normal forces involved in packaging, shipping and shelving so that they maintain their configuration until the same are dispensed by consumers.

Having described preferred embodiments of the invention, it is to be understood that the invention is not limited to those precise embodiments, and that various changes and modifications mat be effected therein by one of skill in the art without departing from the scope or spirit of the invention as defined in the appended claims, which are listed after Tables 1 and 2, each of which is expressly incporporated herein by reference as part of the specification and detailed description of preferred embodiments of the present invention.

TABLE 1

DUAL SPIRAL-BODY LOTION

| INGREDIENTS | WT/WT % |
|---|---|
| WATER | 51.50-85.00 |
| THICKENERS | 1.10-1.00 |
| CHELATING AGENTS | 6.10-1.00 |
| PRESERVATIVES | 0.10-1.00 |

TABLE 1-continued

DUAL SPIRAL-BODY LOTION

| INGREDIENTS | WT/WT % |
|---|---|
| UV-ABSORBERS | 0.10-1.00 |
| HUMECTANTS | 2.00-6.00 |
| VITAMINS | 0.10-1.00 |
| ESTERS | 4.00-0.00 |
| EMULSIFIERS | 1.00-4.00 |
| FATTY ALCOHOLS | 1.00-4.00 |
| FILM FORMERS | 1.00-4.00 |
| SILICONES | 4.00-10.00 |
| POLYTRAPS | 1.00-4.00 |
| DIMETHICONES | 0.50-1.50 |
| TOTAL 100% | |

TABLE 2

SPECIAL PRODUCT-BODY GEL

| INGREDIENTS: | WT/WT % |
|---|---|
| WATER | 62.50-91.85 |
| CARBOMER | 0.40-1.00 |
| PRESERVATIVES | 0.05-1.00 |
| HUMECTANTS | 1.00-6.00 |
| CHELATING AGENT | 0.10-1.00 |
| UV-ABSORBERS | 0.10-1.00 |
| MOISTURIZER/CONDITIONERS | 0.50-3.00 |
| SURFACTANTS | 0.10-1.00 |
| POLYMETHACRYLATES | 5.00-20.00 |
| DIMETHICONES | 0.70-1.50 |
| VITAMINS | 0.10-1.00 |
| HEAVY METALS | 0.10-1.00 |
| TOTAL 100% | |

What is claimed is:

1. A readily flowable composition having a swirled shape contained in a generally transparent container, wherein the swirled composition comprises two substantially dispersed phases of similar viscosity with substantial phase separation at all points of contact between the two phases, and wherein the first phase comprises:

from about 51.5 to about 85.0 percent by weight water;

from about 1.0 to about 1.1 percent by weight thickeners;

from about 0.5 to about 1.5 percent by weight dimethicones;

from about 1.0 to about 4.0 percent by weight fatty alcohols;

from about 4.0 to about 10.0 percent by weight silicones; and from about 1.0 to about 4.0 percent by weight emulsifiers, and wherein the second phase comprises:

from about 62.5 to about 91.85 percent by weight water;

from about 0.4 to about 1.0 percent by weight carbomer;

from about 0.7 to about 1.5 percent by weight dimethicones;

from about 0.1 to about 1.0 percent by weight surfactant; and from about 5.0 to about 20.0 percent by weight polymethacrylates, and wherein at least one of the phases contains a colorant and wherein the phase separation boundary between the two phases promotes product stability by limiting the ability of the phases to mix with one another so that the article of manufacture having the swirled composition has a stable shelf life of approximately 6 months.

2. The composition as recited in claim 1, wherein at least one of the phases further comprises a moisturizing and conditioning ingredient selected from the group consisting of vitamins, antioxidants, pH modifying agents, moisturizing agents, astringents, skin lubricants and emollients.

3. The composition as recited in claim 1, wherein the first phase further includes from about 2.0 to about 6.0 percent by weight humectants.

4. The composition as recited in claim 1, wherein the first phase further includes from about 0.10 to about 1.0 percent by weight chelating agents.

5. The composition as recited in claim 1, wherein the first phase further includes from about 0.10 to about 1.0 percent by weight preservatives.

6. The composition as recited in claim 1, wherein the first phase further includes from about 0.10 to about 1.0 percent by weight uv-absorbers.

7. The composition as recited in claim 1, wherein the first phase further includes from about 0.1 to 1.0 percent by weight vitamins.

8. The composition as recited in claim 1, wherein the first phase further includes from about 1.0 to about 4.0 percent by weight film formers.

9. The composition as recited in claim 1, wherein the first phase further includes from about 1.0 to about 4.0 percent by weight polytraps.

10. The composition as recited in claim 1, wherein the first phase further includes about 4.0 percent by weight of an ester.

11. The composition as recited in claim 1, wherein the second phase further includes from about 0.05 to about 1.0 percent by weight preservatives.

12. The composition as recited in claim 1, wherein the second phase further includes from about 0.1 to about 1.0 percent by weight chelating agents.

13. The composition as recited in claim 1, wherein the second phase further includes from about 0.1 to about 1.0 percent by weight uv-absorbers.

14. The composition as recited in claim 1, wherein the second phase further includes from about 1.0 to about 6.0 percent by weight humectants.

15. The composition as recited in claim 1, wherein the second phase further includes from about 0.1 to about 1.0 percent by weight vitamins.

16. The composition as recited in claim 1, wherein the second phase further includes from about 0.1 to about 1.0 percent by weight heavy metals.

17. The composition as recited in claim 1, wherein the second phase further includes from about 0.5 to about 3.0 percent by weight moisturizers and conditioners.

18. The composition as recited in claim 1, wherein said colorant is selected from the group consisting of colored mica, chlorophyll, carrot oil and metallic based colorants.

19. The composition as recited in claim 18, wherein said metallic based colorants are selected from the group consisting of copper, zinc, chromium, manganese and iron colorants.

20. A readily flowable composition having a swirled shape contained in a generally transparent container, wherein the swirled composition comprises two substantially dispersed phases of similar viscosity with substantial phase separation at all points of contact between the two phases, wherein one phase is an emulsion phase and the other is a gel phase, and wherein the emulsion phase consists of:

from about 51.5 to about 85.0 percent by weight water;

from about 1.0 to about 1.1 percent by weight thickeners;

from about 0.5 to about 1.5 percent by weight dimethicones;

from about 1.0 to about 4.0 percent by weight fatty alcohols;

from about 4.0 to about 10.0 percent by weight silicones;

from about 2.0 to about 6.0 percent by weight humectants;

from about 0.10 to about 1.0 percent by weight chelating agents;

from about 0.10 to about 1.0 percent by weight preservatives;

from about 0.10 to about 1.0 percent by weight uv-absorbers;

from about 0.1 to 1.0 percent by weight vitamins;

from about 1.0 to about 4.0 percent by weight film formers;

from about 1.0 to about 4.0 percent by weight polytraps;

about 4.0 percent by weight of an ester; and from about 1.0 to about 4.0 percent by weight emulsifiers, and wherein the gel phase consists of:

from about 62.5 to about 91.85 percent by weight water;

from about 0.4 to about 1.0 percent by weight carbomer;

from about 0.7 to about 1.5 percent by weight dimethicones;

from about 0.1 to about 1.0 percent by weight surfactant;

from about 5.0 to about 20.0 percent by weight polymethacrylates;

from about 0.05 to about 1.0 percent by weight preservatives;

from about 0.1 to about 1.0 percent by weight chelating agents;

from about 0.1 to about 1.0 percent by weight uv-absorbers;

from about 1.0 to about 6.0 percent by weight humectants;

from about 0.1 to about 1.0 percent by weight vitamins;

from about 0.1 to about 1.0 percent by weight heavy metals; and from about 0.5 to about 3.0 percent by weight moisturizers and conditioners, and wherein at least one of the phases contains a colorant and wherein the phase separation boundary between the two phases promotes product stability by limiting the ability of the phases to mix with one another so that the article of manufacture having the swirled composition has a stable shelf life of approximately 6 months.

21. The composition as recited in claim 20, wherein said colorant is selected from the group consisting of colored mica, chlorophyll, carrot oil and metallic based colorants.

22. The composition as recited in claim 21, wherein said metallic based colorants are selected from the group consisting of copper, zinc, chromium, manganese and iron colorants.

23. The swirled composition as recited in claim 20, wherein the swirled shape is selected from the group consisting of a double helix, a twisted helix, an inverted helix and a combination thereof.

* * * * *